United States Patent [19]

Pich et al.

[11] Patent Number: 4,797,287

[45] Date of Patent: Jan. 10, 1989

[54] CYLINDRICAL MICROTABLETS

[75] Inventors: Claus H. Pich; Thomas Moest, both of Moorrege, Fed. Rep. of Germany

[73] Assignee: BASF Aktiengesellschaft, Ludwigshafen, Fed. Rep. of Germany

[21] Appl. No.: 45,194

[22] Filed: Apr. 30, 1987

Related U.S. Application Data

[63] Continuation of Ser. No. 745,960, Jun. 18, 1985, abandoned.

[30] Foreign Application Priority Data

Jun. 19, 1984 [DE] Fed. Rep. of Germany ....... 3422619
Jun. 19, 1984 [DE] Fed. Rep. of Germany ....... 8418439

[51] Int. Cl.$^4$ ............................................... A61K 9/20
[52] U.S. Cl. ................................................... 424/464
[58] Field of Search .......................................... 424/464

[56] References Cited

U.S. PATENT DOCUMENTS

| 3,175,521 | 3/1965 | Hershberg | 424/14 |
| 3,473,490 | 10/1969 | Corvi-Mora | 107/54 |
| 4,294,819 | 10/1981 | Tencza | 424/14 |
| 4,339,428 | 7/1982 | Tencza | 424/21 |

FOREIGN PATENT DOCUMENTS

| 996819 | 6/1965 | United Kingdom | 424/14 |
| 1204580 | 9/1970 | United Kingdom | 424/37 |
| 2039737 | 8/1980 | United Kingdom | . |
| 2091554 | 8/1982 | United Kingdom | 424/14 |

*Primary Examiner*—Shep K. Rose
*Attorney, Agent, or Firm*—Keil & Weinkauf

[57] ABSTRACT

Cylindrical microtablets which have a convex upper face and a convex lower face and whose cylinder diameter and height independently of one another are each from 1.0 to 2.5 mm and the ratio of the said diameter to said height is from 1:0.5 to 1:1.5, and a process for their preparation.

2 Claims, 1 Drawing Sheet

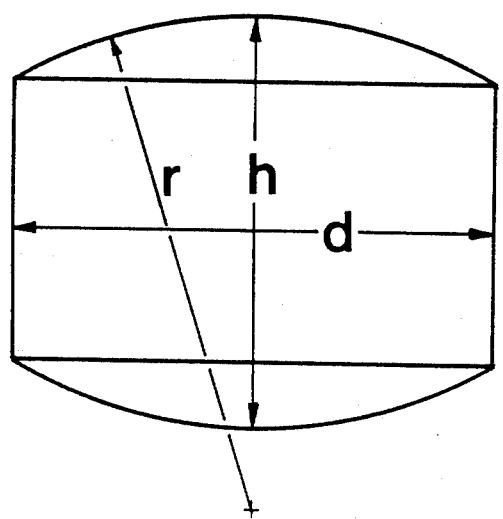

CYLINDRICAL MICROTABLETS

This application is a continuation of application Ser. No. 745,960, filed on June 18, 1985 now abandoned.

For many purposes, it is desirable to have particles 1–2.5 mm diameter which possess a very uniform particle size and regular shape, high weight uniformity, very low porosity, a reproducible surface structure and a high content of active substance. For example, the administration of drugs in the form of pellets which can be introduced into, for example, capsules is generally preferred to the administration of compact tablets because very high local concentrations of active compound in the gastrointestinal tract are avoided with multi-unit-dose-system pellets, in contrast to single-unit-dose-system tablets. However, uniform filling of capsules necessitates uniform size and shape of the pellets. Moreover, the very steady release of active compound per unit time generally desired in the case of sustained-release pellets is only possible if the pellets are of uniform size and shape. The same applies to pellets which are provided with a coating resistant to gastric juice. Only regularly shaped particles permit uniform coating with a very small amount of coating agent.

It is also desirable to prepare pellets which have the stated properties and are of such uniformity that single-unit doses are possible. This means that each individual pellet particle must meet the requirements set by the European pharmacopeia with regard to the single-unit dose forms described there. The necessary weight uniformity for tablets is specified in the European pharmacopeia, vol. III, page 77.

The specifications regarding the disintegration times for uncoated tablets (loc.cit page 235), of coated tablets which are soluble in gastric juice (loc.cit page 237) and of tablets which are provied with a coating resistant to gastric juice (loc.cit page 237) must be met by each pellet particle.

Pellets are usually produced by a pelletizing process, for example using a disk or drum pelletizer, in a coating pan or with the aid of other apparatuses for agglomerative granulation, or by extrusion, cutting of the extrudates and rounding off the resulting cylindrical particles on appropriate conventional apparatuses. These processes are described, for example, by R. Voigt, in Lehrbuch der pharmazeutischen Technologie, 2nd edition, VEB Verlag Volk und Gesundheit, Berlin 1975, 158–169, and in Hagers Handbuch der pharmazeutischen Praxis, 4th edition, Springer-Verlag, Berlin - Heidelberg - New York, 1971, VII A, 312–318.

All of these processes have the disadvantage that they give a broad particle size distribution, so that oversize and undersize particles have to be separated off. Moreover, the shape and/or the surface structure are frequently non-uniform. In all of these processes, a solvent is incorporated and then evaporated, so that a porous structure is produced. The weight of the individual particles fluctuates greatly. Single-unit doses are impossible since the requirements of the European pharmacopeia are not met.

These disadvantages are overcome if tablets are produced by pressing, but tablets having a diameter of less than 3 mm are unknown to date.

Skilled workers from the manufacturing sector for tableting presses and tools, i.e. dies and punches, are unanimous in the opinion that it is impossible to produce smaller tablets. The reasons for this are the sensitivity of the thin punches, which are compressed and break off when used in conventional presses, the required precision of the tableting presses, and the requirements with respect to the free-flowing properties, particle size and particle size distribution of the tableting material.

It is an object of the present invention to produce particles having the properties described at the outset.

We have found that this object is achieved by a process for the production of cylindrical microtablets which have a convex upper face and a convex lower face and whose cylinder diameter and height, independently of one another, are each from 1.0 to 2.5 mm, preferably from 2.0 to 2.3 mm, and their ratio is from 1:0.5 to 1:1.5, preferably from 1:0.9 to 1:1.1, wherein a free-flowing tableting material having a maximum particle diameter of 30%, preferably 20%, of the tablet diameter and containing less than 10, preferably less than 5, per cent by weight of dust (with particle diameters of less than 50 $\mu$m) is pressed with a force of from 0.4 to 3, preferably from 1 to 2, kN.

The required tableting materials having the stated particle size and the stated low dust content are advantageously obtained by milling larger particles, preferred mills being those which have a low shearing action. The process furthermore requires novel tableting presses unlike those available commercially to date. Not only must they possess correspondingly small dies and punches, but the measuring range for the applied compressive force must be adapted to the smaller dimensions of the microtablet. The tools must be controlled in a particularly precise manner. Sensitive control of the metering is required in order to avoid deviations of the mean tablet weight during the pressing procedure, since overfilling the dies leads to overloading of the tools. Finally, it is necessary to provide a very efficiently functioning scraper, which conveys the microtablets carefully and without damage, but also reliably without leaving a residue, from the die into the discharge device.

The radius of curvature r of the convex upper and lower faces of the cylindrical microtablet is from 0.6 to 1.5 times, preferably from 0.7 to 0.9 times, the diameter of the cylinder. With smaller radii of curvature (a spherical shape), the tools do not withstand the pressure required, while with larger radii flat upper and lower faces (infinite radius of curvature) are approached, with the disadvantage that the edges present problems during coating and are susceptible to mechanical damage.

The height of the tablet is the maximum dimension along the cylinder axis.

Free-flowing, as used herein, is intended to mean that the cotangent $\psi$ of the angle of slope determined in accordance with DIN 53916 is greater than 1.2, preferably greater than 1.4.

The term dust content, as used herein, embraces the product fractions having particle diameters of less than 50 $\mu$m. The amount of such fractions in the material being pressed should be less than 10, preferably less than 5, per cent by weight.

Pharmaceutical microtablets contain one or more active pharmaceutical compounds in an effective amount, in addition to conventional pharmaceutical auxiliaries.

The novel microtablets weigh from 1 to 20, preferably from 5 to 10, mg. The relative standard deviations of the mean weights of 50 weighed microtablets prepared by this process are less than 4%, in general even less than 2.5%. They meet the requirements of the European pharmacopeia in respect of weight uniformity of tablets. For a definition of the standard deviation, see textbooks of statistics, eg. Siegfried Noack, Auswertung von Mess- und Versuchsdaten mit Taschenrechner und Tischkomputer, Walter de Gruyter Verlag, Berlin, New York 1980, pages 192–201.

After having been provided with a retarding lacquer coating, conventional pellets of non-uniform size and shape give characteristics for the release of active compound which exhibit pronounced scatter in individual cases. This is attributable to the different surface areas of pellets which have different diameters.

Smaller pellets which have a large surface area per unit weight require a larger amount of coating material than larger pellets with a smaller surface area per unit weight, in order to produce a coating which has the same thickness and is thus equally effective. This broad distribution of release rates is reinforced by the effects of shape factors, since particles with edges and corners or raised surface structures require a larger amount of coating material in order to cover these irregularities.

When an average amount of surface coating material is applied during the coating procedure, only a few pellets will achieve the desired average release characteristics. Release from large and flat particles will be slower, and that from small and irregular particles will be faster.

Mixing these different particles leads to addition of the individual release characteristics and hence to pronounced deviation from the desired linear characteristics. 0-order release is not possible in the case of a large number of simultaneously releasing pellets, as are present, for example, after a hard gelatine capsule has been dissolved.

If the novel microtablets are provided with a retarding coating by a conventional method, for example by fluidized-bed coating or by coating in a perforated drum coater with coating solutions based on, for example, ethylcellulose or acrylic resins, the uniformity of size, shape and surface structure of the microtablets leads to coatings which ensure that each retard pellet releases the active compound present at a steady rate. A pellet ensemble, e.g. the contents of a hard gelatine capsule, has the same narrow-band release characteristics, i.e. linear variation with time.

The skilled worker is familiar with the problem of using coatings which are soluble in intestinal juice to formulate conventional pellets resistant to gastric juice so that the active compound present in the pellets is reliably protected from the action of the acidic medium in the stomach. Protection from gastric acid is necessary particularly for acid-sensitive substances, e.g. the enzyme lipase. In the case of pellets of this type, a coating which is resistant to gastric juice usually requires a very large amount of coating material, which accounts for as much as 50% of the total weight of the coated pellets. Nevertheless, such resistant pellets too are generally only resistant to gastric juice in the sense that the active compound does not diffuse through the coating and into the gastric acid, but not in the required way whereby the gastric acid is not diffused in the opposite direction through the coating and into the interior of the pellet.

With the novel microtablets, pellets which are completely resistant to gastric juice can be produced without particular expense. With the aid of the abovementioned coating procedures, pellets which are homogeneously resistant to gastric juice can be obtained by applying coatings based on conventional coating systems, such as cellulose acetate phthalate or hydroxypropylmethylcellulose phthalate. The consumption of coating material is not more than 25% (w/w), depending on the pellet size; in many cases 10% (w/w) is sufficient.

The novel microtablets can consist of a very wide range of materials and accordingly can be used for a very large variety of purposes. For example, they can be employed as catalysts in the petroleum and chemical industries, or as readily meterable starting materials or additives for solutions as used in a very wide variety of industrial processes, for example for finishing and dyeing textiles, tanning, impregnation, etc. However, the most important and very particularly preferred field of use is in the pharmaceutical sector. Their advantages are particularly utilized when they are provided with a retarding or gastric juice-resistant coating. Retardation can be effected by the matrix principle or, preferably, by means of a coating. The very particularly preferred novel microtablets provided with a coating resistant to gastric juice are those which contain pancreatin as the active compound.

Surprisingly, not only is it possible to produce microtablets having a diameter of less than 2.5 mm by pressing, but these microtablets furthermore possess unexpectedly good pressing characteristics, and the pressability of materials intended for pressing is, surprisingly, better in the case of such small tablets.

For example, it is possible to produce microtablets having a high content of substances which are difficult to press.

Paracetamol can be pressed, via PVP granules, to give mechanically stable microtablets containing 95% of active compound. These are so stable that they can be coated in a Wurster apparatus.

10 mm tablets prepared from the same granules by way of comparison cannot be coated since they undergo laminar cleavage under mechanical load.

This cannot be prevented by means of a higher compressive pressure, this resulting, on the contrary, in direct capping.

The mold release agent talc can likewise be pressed via PVP granules to give firm microtablets having a content of 95%. These microtablets, too, are so stable that they can be coated without difficulty in a Wurster apparatus.

10 mm tablets prepared from the same granules by way of comparison possess only little strength. When they are fluidized in the Wurster apparatus, the mechanical abrasion is sufficient to cause the tablets to lose their shape.

Pancreatin can be pressed to give tablets having a content of 99.5%.

If these granules are pressed using conventional round tools of 10 mm diameter, either capping is observed or the strength of the resulting tablets is insufficient to permit them to be further processed.

In the Examples, parts and percentages are by weight.

EXAMPLE 1

Commercial coarse-particled ascorbic acid which met the requirements of the pharmacopeia was comminuted on a roll mill so that 1.2% remained on a sieve having a mesh size of 0.4 mm. The fraction below 50 $\mu$m was 7.5%

1,940 g of this milled vitamin C were mixed with 50 g of microcrystalline cellulose and 10 g of magnesium sterate in a 5 liter mixer. The mixture, having free-flow characteristics according to DIN 53916 which corresponded to cotangent $\psi = 1.45$, was pressed on an eccentric press equipped with instrumentation and having precise punch control to give microtablets having a diameter of 1.5 mm and a height of 1.8 mm, the compressive force used being 0.9 kN. The radius of curvature was 1.0 mm.

The mean weight of 50 microtablets was 3.56 mg, the relative standard deviation being 2.9%. The microtablets met the pharmacopeia requirements in respect of weight uniformity for tablets.

After 300,000 microtablets had been prepared, the press tool still remained completely undamaged.

EXAMPLE 2

The oversize was removed from commercial potassium chloride which met the pharmacopeia requirements by means of a 0.5 mm sieve. The fine fraction contained 2.7% of just having a size of less than 50 μm.

After 11,940 g of this potassium chloride fraction has been mixed with 60 g of magnesium stearate in a 50 liter mixer, the mixture had free-flow characteristics according to DIN 53916 which corresponded to cotangent $\psi = 1.49$.

This material for pressing was converted to pellet-like microtablets having a diameter of 2.0 mm and a height of 2.0 mm on a 24-punch rotary press with sensitive monitoring of the compressive force and control of metering, and with a very precisely operating scraper, the compressive force used being 1.5 kN. The radius of curvature was 1.4 mm, the mean weight of 50 microtablets was 11.2 mg and the relative standard deviation was 1.8%.

The microtablets met the pharmacopeia requirements for weight uniformity for tablets. After the preparation of 100,000 microtablets, the press tool was still undamaged.

The potassium chloride microtablets were coated continuously in a fluidized-bed spray granulator with an ethanolic ethylcellulose solution whose concentration was 5.5% (w/w). The specific viscosity of the ethylcellulose was 10 mPas. The polymer solution contained 20%, based on the weight of the polymer, of dibutyl phthalate as a plasticizer.

Talc was suspended in this solution, as a filler, in an amount of 50% (w/w), based on the weight of the polymer. The total amount of coating material was 5% (w/w), based on the coated potassium chloride microtablets. The fluidized-bed coating procedure was controlled so that the product temperature was from 23° to 25° C.

Filling of the retarded potassium chloride microtablets produced in this manner into hard gelatine capsules could be carried out very easily and precisely in conventional apparatuses.

Potassium chloride release as determined by the paddle method according to U.S. pharmacopeia XX showed the following behavior:

| Time (h) | Amount liberated in % |
|---|---|
| 1 | 14 |
| 2 | 30 |
| 4 | 62 |
| 8 | 98 |

COMPARATIVE EXPERIMENT

For comparison, potassium chloride pellets were prepared on a disk pelletizer, 4% (w/w) of hydroxypropylmethylcellulose being incorporated as a binder, and undersize particles smaller than 1.6 mm and oversize particles larger than 2.0 mm were separated off by means of a sieve. The useful fraction was retarded by a similar process, the total amount of coating material being 5.5% (w/w) based on the coated potassium chloride pellets.

Release of potassium chloride gave the following values:

| Time (h) | Amount liberated in % |
|---|---|
| 1 | 27 |
| 2 | 46 |
| 4 | 60 |
| 8 | 93 |

Comparison of the two products showed that the retarded potassium chloride microtablets used according to the invention approach ideal behavior, i.e. 0-order release, whereas the conventionally prepared potassium chloride exhibits substantial deviations.

EXAMPLE 3

Pancreatin prepared by the extraction method was comminuted on a roll mill so that the fraction above 0.5 mm was 0.8%, and the dust fraction below 50 μm was 3.5%.

After 1,990 g of this pancreatin had been mixed with 10 g of magnesium stearate in a 5 liter laboratory mixer, the mixture had free-flow characteristics according to DIN 53916 which corresponded to cotangent $\psi = 1.35$.

This material for pressing was converted to microtablets having a diameter of 2.25 mm and a height of 2.2 mm on an eccentric press equipped with instrumentation, and having precise punch control, the compressive force used being 2 kN. The radius of curvature was 1.7 mm. The mean weight of 50 microtablets was 8.5 mg and the relative standard deviation was 2.4%.

The microtablets met the pharmacopeia requirements in respect of weight uniformity for tablets.

The pancreatin microtablets were coated in a rotating perforated drum (Accela Cota 24" from Manesty, Liverpool having a drum with 0.3 mm perforations produced by laser beam) with a solution of hydroxypropylmethylcellulose phthalate in a 3:7 isopropanol/methylenechloride mixture with the aid of a two-material nozzle. The concentration of the solution was 7% (w/w). The total amount of the coating polymer was 14% (w/w), based on the coated pancreatin microtablets. 20% (w/w), based on the polymer material, of dibutyl phthalate was added to the polymer solution, as a plasticizer.

The coating procedure was controlled so that when the coating solution was metered at a rate of 40 ml/min, the product temperature remained at 24°-26° C.

The pancreatin microtablets resistant to gastric juice could be introduced into hard gelatine capsules very easily and precisely using conventional apparatuses.

The resistance to gastric juice was tested by the method described in Ph. Eur. Furthermore, the penetration of synthetic gastric acid into the pellets was determined by measuring the content of lipase after the acid had been allowed to act for 2 hours, and comparing this content with the initial value.

In the microtablets resistant to gastric juice and produced according to the invention, no decrease in the lipase activity could be detected.

For comparison a commercial product containing pellets resistant to gastric juice was investigated. Although this product was resistant to gastric juice according to the pharmacopeia specification, the lipase activity was found to decrease by 60% after exposure to synthetic gastric acid for 2 hours. The amount of coating in this product was determined as 38% (w/w).

To compare the tabletting behavior, circular 10 mm tablets were prepared from the same material for pressing, containing 99.5% of pancreatin.

These tablets possess only a low breaking strength and exhibit high abrasion. An attempt to coat them in a Wurster apparatus had to be terminated because fragments and particles produced by abrasion did not permit useful coating to be carried out.

EXAMPLE 4

Finely powdered active carbon was granulated in an intensive mixer, together with starch paste, prepared by heating 10% of corn starch in water. The amount of starch paste was 15% (w/w). The moist granules were passed through a sieve of 1.6 mm mesh size, dried in a drying oven and then comminuted in a suitable mill so that the fraction above 0.5 mm was 2.8% and the dust fraction below 50 μm was 1.4%.

These granules were mixed with 3% of talc to give a mixture having free-flow characteristics according to DIN 53916 which corresponded to cotangent $\psi = 1.6$.

This material for pressing was converted to microtablets having a diameter of 2.0 mm and a height of 2.5 mm on a 24-punch rotary press with sensitive monitoring of the compressive force and control of metering and with a precisely operated scraper, the compresive force used being 1.5 kN. The radius of curvature was 1.4 mm, the mean weight of 50 microtablets was 8.2 mg and the relative standard deviation was 2.5% the microtablets met the pharmacopeia requirements in respect of weight uniformity for tablets.

EXAMPLE 5

Coarse-particled propafenone was comminuted using a roll mill so that the fraction above 0.6 mm was 0.2% and the dust fraction below 50 μm was 0.9%.

When 1,600 g of this propafenone had been mixed with 250 g of microcrystalline cellulose, 100 g of lactose, 40 g of talc and 10 g of magnesium stearate in a 5 liter laboratory mixer, the resulting mixture had free-flow characteristics according to DIN 53916 which corresponded to cotangent $\psi = 1.5$.

This material for pressing was converted to microtablets having a diameter of 2.1 mm and a height of 2.0 mm on an eccentric press equipped with instrumentation, and having precise punch control, the compressive force used being 1.5 kN. The radius of curvature as 1.5 mm. The mean weight of 50 microtablets was 7.0 mg and the relative standard deviation was 1.5%.

The propafenone microtablets were coated continuously, in a fluidized-bed spray granulator having a Wurster insert, with a 20% strength (w/w) aqueous solution of hydroxypropylmethylcellulose (specific viscosity 3 mPas). The total amount of the coating polymer was 5% based on the coated propafenone microtablets. The coating procedure was controlled so that the product temperature remained at 31°–34° C.

EXAMPLE 6

Iron(III) oxide powder for catalytic purposes was granulated with a 20% strength (w/w) aqueous solution of polyvinylpyrrolidone (specific viscosity K=25) in an intensive mixer. The moist granules were passed through a sieve of 2 mm mesh size, dried in a drying oven and then comminuted using a roll mill so that the fraction above 0.5 mm was 3.4% and the dust fraction below 50 μm was 5.8%. The amount of polyvinylpyrrolidone was 2% (w/w).

These granules were mixed with 2% of graphite to give a mixture having free-flow characteristics according to DIN 53916 which corresponded to cotangent $\psi = 1.4$.

This material for pressing was converted to microtablets having a diameter of 2.25 mm and a height of 2.25 mm on an eccentric press equipped with instrumentation, and having precise punch control, the compressive forced being 1.2 kN. The radius of curvature was 2.0 mm. The mean weight of 50 microtablets was 15.8 mg and the relative standard deviation was 3.5%. The catalyst microtablets could be fluidized in a fluidized bed without any noticeable mechanical abrasion.

We claim:

1. A cylindrical pharmaceutical microtablet consisting essentially of pancreatin, said microtablet having a convex upper face and convex lower face, wherein the cylinder diameter and the height independently of one another are each from 1.0 to 2.5 mm, the ratio from the said diameter to the said height being from 1:0.5 to 1:1.5, and the radius of curvature r of the convex upper and lower faces of the cylindrical microtablet is from 0.6 to 1.5 times the diameter of the cylinder.

2. The microtablet of claim 1 having a pancreatin content of 99.5%.

* * * * *